(12) United States Patent
Han

(10) Patent No.: US 6,213,840 B1
(45) Date of Patent: Apr. 10, 2001

(54) HANDS-FREE BREAST PUMP SUPPORTING BRA AND SYSTEM

(76) Inventor: Bonnifant Heeja Han, 5241 Savoy Ct., Cape Coral, FL (US) 33904

( * ) Notice: Subject to any disclaimer, the term of this patent is extended or adjusted under 35 U.S.C. 154(b) by 0 days.

(21) Appl. No.: 08/984,409

(22) Filed: Dec. 3, 1997

(51) Int. Cl.[7] .............................. A61M 1/06; A41C 3/00
(52) U.S. Cl. ................................. 450/36; 2/104; 604/74
(58) Field of Search .................................. 2/73, 69, 69.5, 2/104, 105, 106, 113, 114, 115; 450/36; 604/73–74, 118–119

(56) References Cited

U.S. PATENT DOCUMENTS

| | | |
|---|---|---|
| 4,633,876 * | 1/1987 | Scullin .................................... 450/36 |
| 5,514,166 | 5/1996 | Silver et al. . |
| 5,575,768 | 11/1996 | Lockridge et al. . |

\* cited by examiner

*Primary Examiner*—Jeanette Chapman
(74) *Attorney, Agent, or Firm*—Max Oppenheimer

(57) ABSTRACT

A hands-free breast pump support bra and system allow simple and effective breast milk expression from a lactating woman's breasts without the need of additional support, such as straps, bands, posts and mounting elements to support the weight of breast pump apparatuses. The support bra independently and as part of the system is made of a material of sufficient elasticity and strength that when worn firmly and frictionally holds against each breast the funnel-like portion of a breast pump during the complete breast milk expression operation. Slits are strategically located in both nipple areas of the bra's cups through which the funnel-like portions of breast pumps engage the breasts. Because of the elastic property of the bra's fabric, the fabric around the slits securely and simultaneously hold against each breast in a hands-free manner a funnel portion with a conventional breast milk bottle filled with milk and attached thereto.

11 Claims, 5 Drawing Sheets

HANDS-FREE BREAST PUMP SUPPORTING BRA AND SYSTEM

BACKGROUND OF THE INVENTION

Breast pumps systems for breast milk expression are well known. They use either electric or mechanical means for creating vacuum to aid in breast milk expression. Both types conventionally have funnel portions that are held against a woman's breast to both introduce the vacuum to the nipples and to catch the expressed breast milk. The vacuum draws breast milk from a nipple through the funnel portion to a breast milk container for subsequent use.

Hands-free breast pump support devices are also known. However, these devices have many different parts that make their use very complicated, difficult and time-consuming--rendering them ineffective. U.S. Pat. No. 5,575,768 (Lockridge et al.), which is a continuation-in-part of U.S. Pat. No. 5,514,166 (Silver et al.), discloses such devices.

In addition to a garment (or bra) and a breast pump's funnel portion, the described breast pump support devices of Lockridge et al. further require a plurality of additional elements in order to support a breast pump device: two or more loops or anchoring members attached to the garment; one or more rubber bands attached to the loops; and a mounting element, which may or may not be removably attached to the funnel portion, that has numerous posts to which the band(s) is/are further attached. The use of these devices is so complicated that many women refuse to use them. The problem with these devices is that the garments used cannot independently support a breast pump device by themselves. Indeed these devices must have additional bulky elements to support the weight of even one breast pump device, which make their use overly complicated, difficult and time-consuming even for the most gifted engineer. Furthermore, these additional support elements suffer from the increased cost of using them.

SUMMARY OF THE INVENTION

The principle object of this invention is to provide an inexpensive, easy-to-use, hands-free breast pump supporting bra and system that fully support simultaneously against each breast a funnel portion of a breast pump device with attached conventional breast milk bottle, even when filled with breast milk, without the need of additional support elements such as loops, bands, mounting elements, anchoring members or other support means.

Another object of this invention is to provide a hands-free breast pump support system that can be used in a minimum number of simple and quick steps to minimize the time required to express breast milk.

Another object of this invention is to provide improved hygiene associated with breast milk expression by allowing the system to be conveniently stored as "one-piece" in a refrigerator.

Another object of this invention is to provide a means for conveniently expressing then refrigerating or freezing breast milk for later use.

The breast pump supporting bra, which is used in the claimed system's bra, is made of an elastic material, such as LYCRA or SPANDEX blended with COOLMAX or cotton. In each of the two cup portions of the bra is a slit strategically located where a woman's nipple would lie underneath the fabric when the bra is worn. The funnel portion of the breast pump or the base of the funnel-like portion fits through the slit such that the opening of the funnel portion is facing the woman's breast and the funnel portion's base extends outwardly from the bra. Because the fabric surrounding and defining the slits is elastic, the slit will increase in size when the fabric around it is stretched and subsequently shrink back to its original size after stretching. The size of the slit when stretched must be sufficiently large to accept the smaller of either the funnel-like portion or the funnel-like portion's base.

BRIEF DESCRIPTION OF TIE DRAWINGS

DETAILED DESCRIPTION OF THE INVENTION

Hands-free Breast Pump Supporting Bra

It is best to start with a particular running bra, one that has much more support than a conventional bra and has more support than sports bras with low elasticity. Generally, the bra should have a high degree of elasticity. I used a CHAMPION JOGBRA that is made with the following fabric: Outer shell, 43% cotton, 43% polyester and 14% LYCRA SPANDEX; Inner shell, 56% cotton and 44% polyester; and Wings (the shoulder strap portions and the torso portion) 86% nylon and 14% LYCRA SPANDEX.

Figure 1:
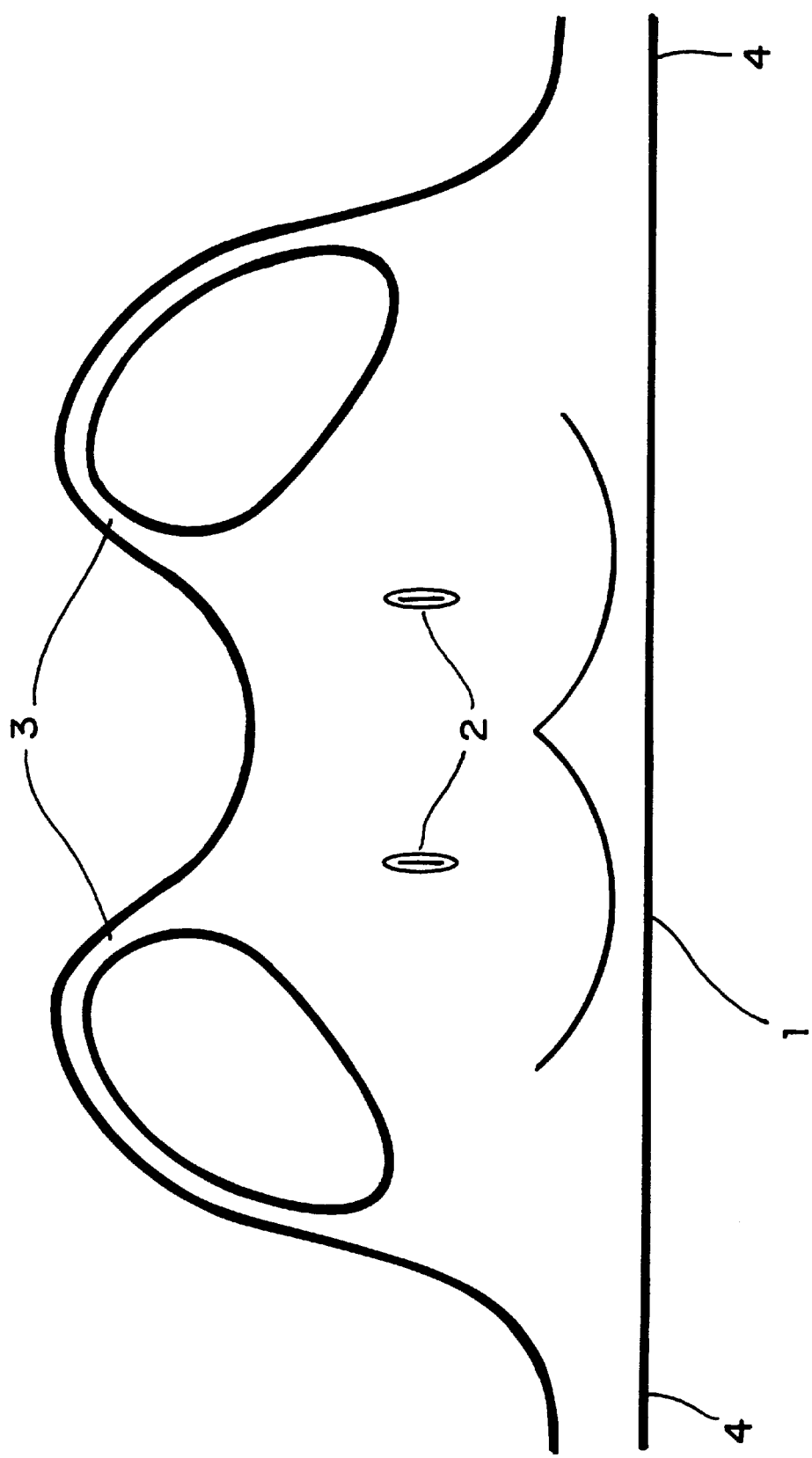
FIG. 1 shows a running bra adapted to support breast pumps.

Referring to FIG. 1, for each cup portion of the running bra 1, cut a 1.5 inch slit 2 in the outer shell right above where the nipples would be if the bra were worn. Note that the inner shell of the CHAMPION JOBBRA is not elastic, and I had to cut a 2.25 inch slit in it for the funnel portion to fit through it. But the outer shell provides more than sufficient elasticity and support to perform the job. My slits are vertical, but horizontal slits can be used instead. Furthermore, any shape and size of cut can work as long as it is big enough for the funnel portion of breast pump to fit through when the fabric around the slit is stretched and small enough to hold the funnel portion against a breast when the fabric, with sufficient elasticity, around the slit is not stretched. The fabric around the slits should be strengthened by hemming the fabric around the slits 2 with elastic thread so it will resist tearing and fraying when the fabric is stretched and as the bra is used. Furthermore, as I noticed on the CHAMPION bra, specific conventional thread patterns and loose sewing techniques facilitate the elasticity of hemmed areas. In fact, almost any type of conventional reinforcing means can be used as long as it does not prevent the fabric around the slits from stretching. I believe that a circle-shaped cut may be best because it may provide the best support. The strap means here is a pair of shoulder straps 3 and a torso strap 4 (Collectively, CHAMPION calls these wings.)

Figure 2:
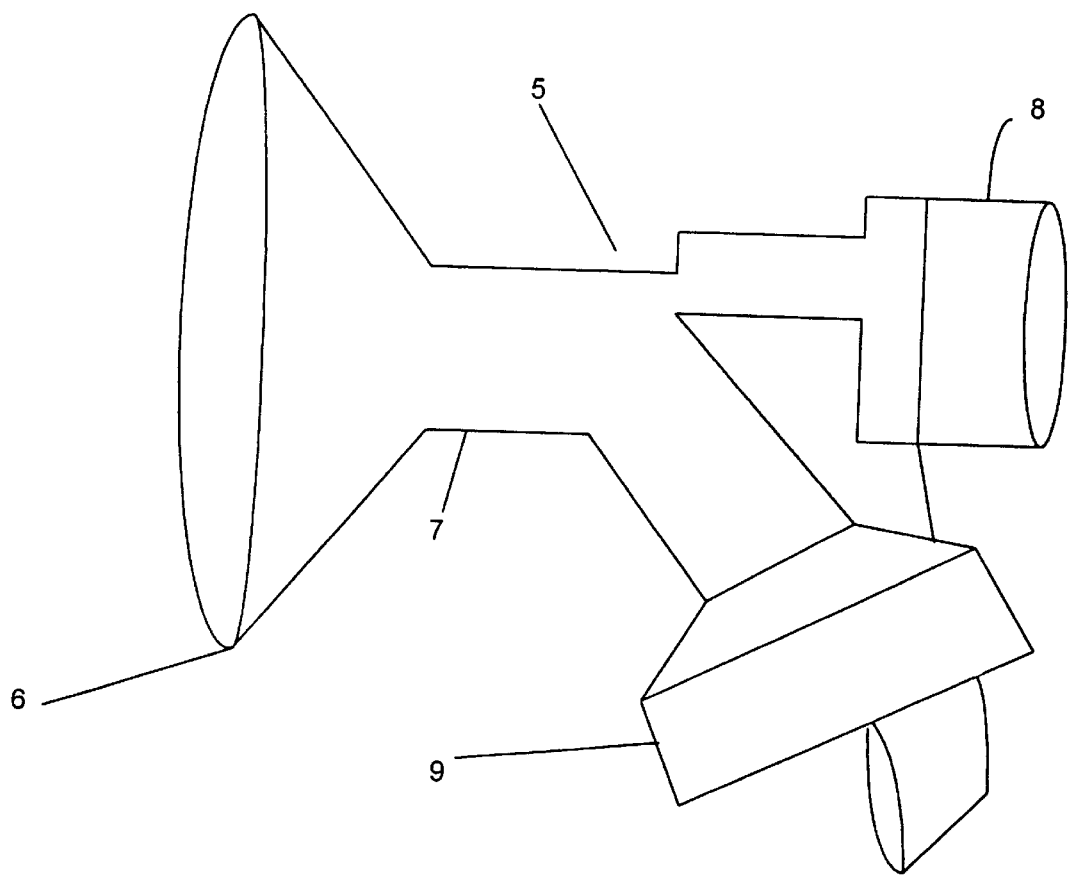
FIG. 2 shows a funnel portion of a conventional breast pump, which also has pump and bottle connectors.

Referring to FIG. 2, I used a conventional MEDELA-brand breast pump's funnel portion 5. But most types of funnel portions of breast pumps will work because the various funnel portions are roughly the same size in circumference and one universal sized slit or opening should work with all of them. If not, slight increases in the size of the slits may be required. This funnel portion has a wide portion 6 and a tube or narrow portion 7. Connected to the narrow portion 7 is the pump connector 8 and the bottle connector 9. Because the narrow portion of the funnel portion, including the connected pump connector 8 and bottle connector 9, could fit through a smaller slit than the wide portion of the funnel portion, I slide the narrow portion of the funnel portion through the slit from the inside of the bra rather than the wide portion through the outside of the bra. This way, the slit can be made smaller with more support from the bra being achieved and less wear on the slit occurring. Yet, the 1.5 inch slit I made is big enough for the wide portion of the funnel portion to slide through, and the bra (specifically, the outer shell) still easily supports the weight of two breast pumps working in a hands-free manner. The 1.5 inch slit provides enough support to additionally support the weight of two attached bottles filled with milk.

If the funnel portion of the breast pump is bigger than conventional ones, a slit larger than 1.5 inches can be made. But some way to make the slit smaller may be required if the bra is to be truly used for hands-free pumping because the slit may be so big that even when not stretched, the fabric around the slit may not provide enough support to hold up the weight of both breast pumps with or without bottles filled with milk. Many methods for doing this can be used, such as a zipper, a draw string, a snap, VELCRO, a button or a piece of fabric connected to the cup portion that can be wrapped around the narrow portion of the funnel portion and then securely attached to the cup portion via a snap, VELCRO, button or other attaching means.

Figure 3:
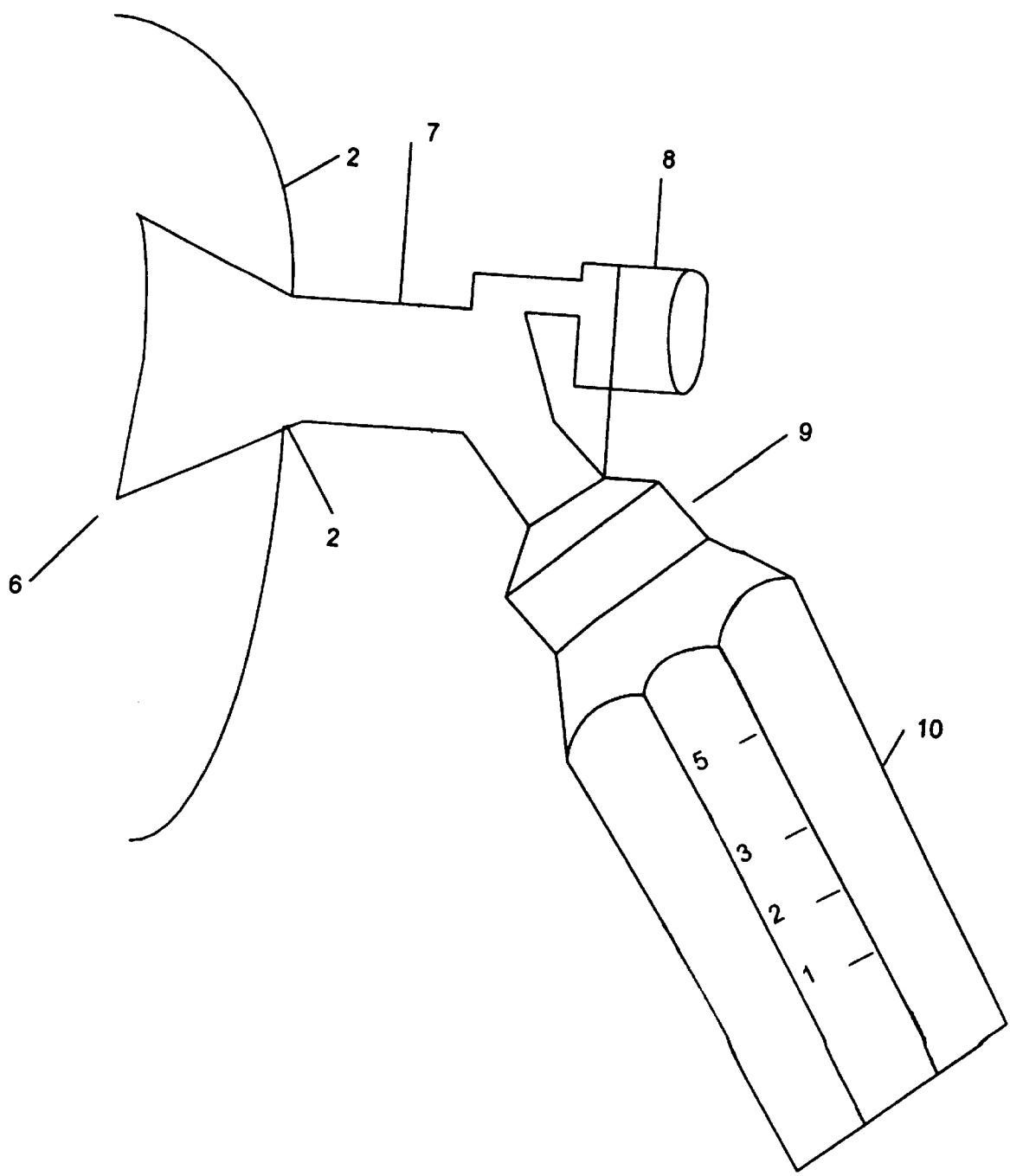
FIG. 3 shows shows a convention breast pump and bottle.
Figure 3B:
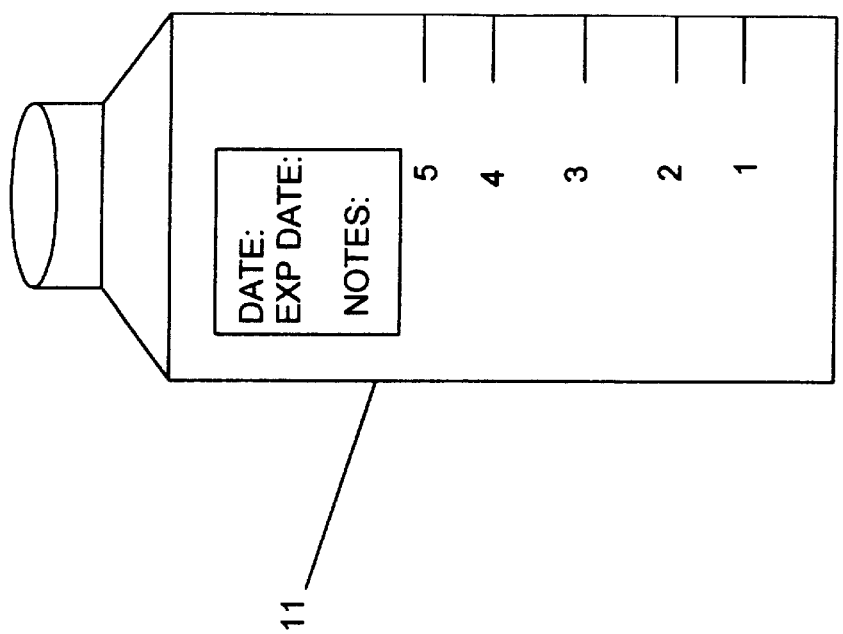
FIG. 3b shows a novel freezer-ready bag for attachment to a funnel portion of a breast pump.
Figure 3A:
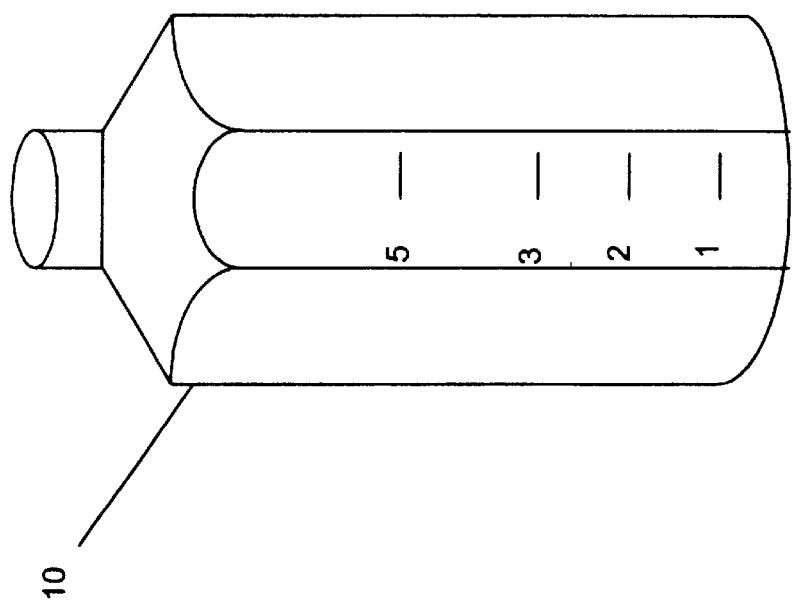
FIG. 3a shows a conventional bottle for attaching to a funnel portion of a breast pump.
Figure 4:
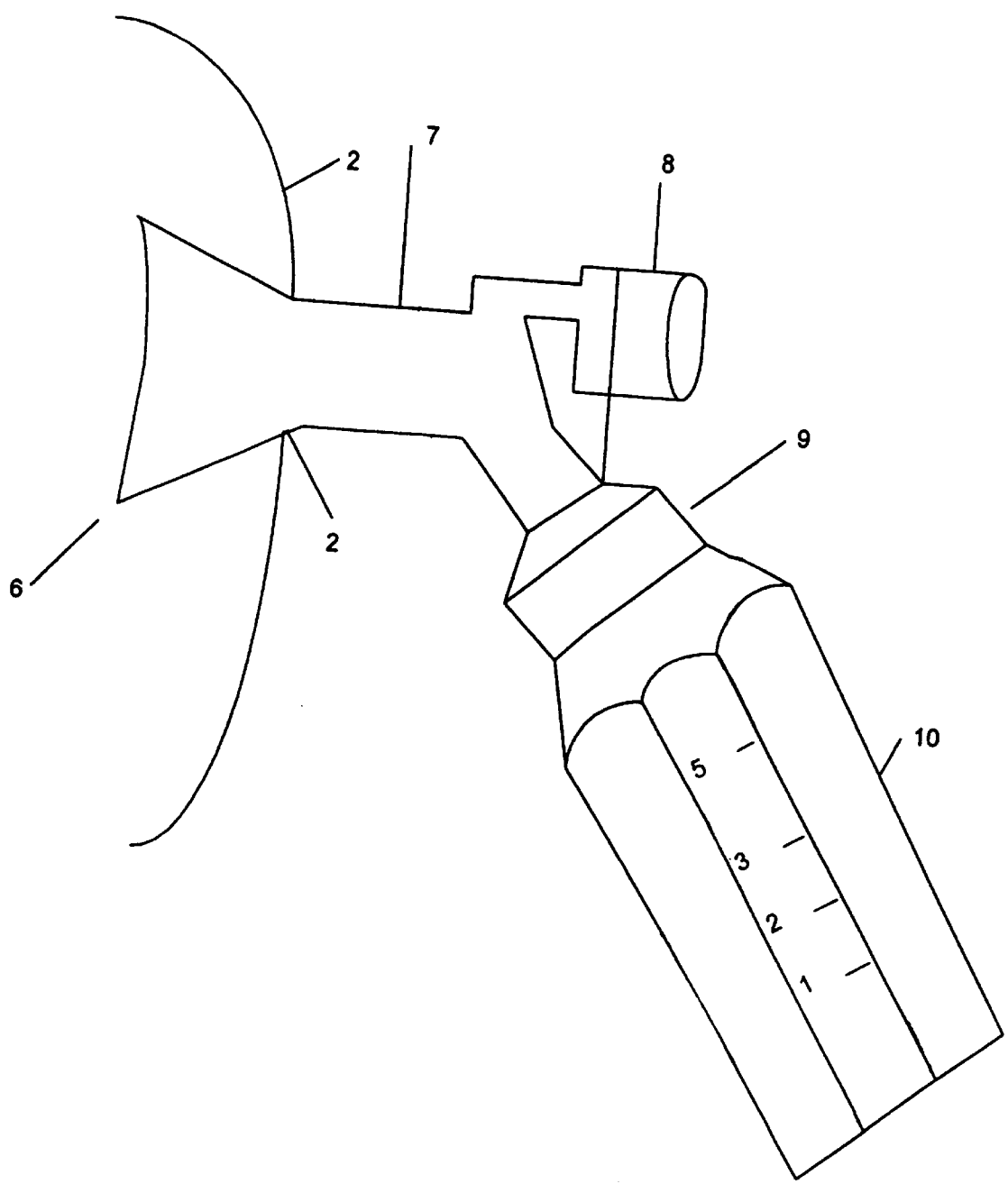
FIG. 4 shows a funnel portion of a conventional breast pump apparatus being operatively supported by a hands-free breast pump support bra.

Referring to FIGS. 1, 3a and 4, the following describes how the breast pump supporting bra works. After I stretch the fabric around each slit 2, I slide the narrow portion or the wide portion of each funnel portion 6 through each slit 2. The wide portions are now on the inside of the bra. The fabric around the slits 2 are gripping against the tubes 7 with the bottle connector 9 and pump connector 8 sticking out from the bra. I put the bra on using the VELCRO on the ends of the torso strap 4. This is fast and simple. I then attach an electrical pump (not shown) to each pump connector 8. I attach a bottle 10 to each bottle connector 9, and just turn on the pump.

Because the bra fully supports the weight of the funnel portion with two filled bottles of milk (up to 10 ounces total), both of my hands are completely free to do many different things.

Hands-free Breast Pump Supporting System

The hands-free breast pump supporting system uses the hands-free breast supporting bra. However, it has three additional features. The first feature is that the funnel portions of the breast pumps are left in the slits even when the system is not being used. The tube or narrow portion 7 that I use has the pump connector 7 and the bottle connector 8 that act as an abutment so that the funnel portion stays in place. However, a particular funnel portion may not have an abutment to keep the funnel portion in place. If this is the case, a post or similar abutment can be attached with glue or similar means or molded to the narrow portion 7 to serve this purpose. In fact, a number of rubber bands can be put around the narrow portion 7 to create such an abutment. Alternatively, the slit can be cut as small as possible to maximize the friction between the fabric surrounding the slit and the narrow portion of the funnel portion.

The second feature is that in addition to bottles, freezer-ready bags with adapters to fit the bottle connector 8 can be used. FIG. 3a shows a conventional breast milk bottle that can be attached to a funnel portion's bottle connector 8. FIG. 3b shows a novel freezer-ready bag that is adapted to fit Medela's funnel portion. But since there are many ways to attach a bottle or bag to a funnel portion, my invention is not limited to using Medela's method. Any obvious way to connect them can be used and any obvious container can be used. By using these bags for catching and holding the expressed milk, the milk can be frozen for later use. This is very convenient, especially when one has a surplus of breast milk.

The third feature stems from the first—the funnel portions being left in the slits. Empty bottles or bags can be attached to the bottle connectors and the entire bra can then be stored in the refrigerator, which makes the bra cold. When a lactating mother is ready to express breast milk, her breasts can be very hot, which is uncomfortable. Putting on the cold bra is not only soothing, but since the funnel portions are already in place with bottles or bags attached, performing milk expression is very quick. All that is needed is for the bra to be put on and the pump attached to the pump connector. Furthermore, after milk expression in completed, new sterile bottles or bags can be attached, the pump detached, and the bra with funnel portions can be immediately stored in a refrigerator. Doing this can reduce how often the funnel portions need to be sterilized. Since many women today work outside of the home, having a system to quickly, conveniently, and hygienically express breast milk is a must.

Additionally, the bra can be made out of a decorative material so it does not look so much like underwear.

Also, the bra can be cut so that it extends down to a woman's waist line. This full length embodiment promotes privacy in that women who express milk with this bra or system in a public bathroom need not expose their skin between their breasts and waist. The strapping means for this full length bra can be a zipper, VELCRO, clasp or similar enclosure means for enclosing the bra around a woman's torso. It can be located anywhere on the bra, but a vertically positioned one located either on one side or down the middle of the front of the bra should be the most convenient and effective.

Therefore, I claim:

1. A hands-free breast pump supporting bra comprising:

a strap means; and two one piece unitary cup portions formed from a unitary single piece of fabric;

wherein said cup portions and strap means are connected to each other;

wherein said strap means straps said bra around a female's torso and shoulders, wherein each of said cup portions is associated with and supports each of a female's breasts, wherein each of said cup portions has a slit opening centered over the nipple of a female wearer when the brassiere is worn and so positioned to operatively allow a breast pump funnel portion access to the nipple of its associated breast; each of said slit openings being of an original size of at least 1.5 inches; wherein said original size is larger than a female nipple but smaller than the female breast; said slit opening is formed from the said unitary piece of fabric of the said cup portions; and wherein the fabric surrounding and defining each of said openings is made of an elastic material such that the opening is enlarged when the fabric around the opening is stretched and subsequently shrinks back to its original size when the fabric is not stretched.

2. The bra of claim 1 wherein said strap means comprises two shoulder strap portions and a torso strap portion, wherein said strap and torso portions are made of an elastic fabric and are adjustable.

3. The bra of claim 1 wherein said bra contains up to 100% elastic fabric.

4. The bra of claim 1 wherein said fabric of said bra is decorative.

5. The bra of claim 2 wherein said shoulder and torso straps are wider than a bra for the purpose of providing greater breast pump and breast support, and are conventionally adjustable.

6. The bra of claim 2 wherein said torso strap has two open ends and said open ends are removably attached to each other by VELCRO™.

7. The bra of claim 1 wherein reinforcing means is used around a rim of said fabric surrounding and defining said openings to strengthen said fabric and to prevent said fabric from tearing and fraying.

8. The bra of claim 1 wherein said bra, when worn, covers a woman's torso down to her waist.

9. The bra of claim 8 wherein said strap means includes an enclosure means.

10. A combination brassiere and breast pump-supporting system comprising:

at least one breast pump apparatuse;

at least one breast milk container;

a strap means, and two one piece unitary cup portions formed from a unitary single piece of fabric;

wherein a breast pump apparatus comprises a funnel portion and a pumping means, and said funnel portion, pumping means and a breast milk container operatively attach to each other and interrelate to express breast milk from a lactating female's breast by vacuum means and directs it into a breast milk container, wherein said funnel portion has a wide portion and a narrow portion, said narrow portion having an abutment means;

wherein said cup portions and strap means are connected to each other;

wherein said strap means straps said bra around a female's torso and shoulders, wherein each of said cup portions is associated with and supports each of a female's breasts, wherein each of said cup portions has a slit opening centered over the nipple of a female wearer when the brassiere is worn and so positioned to operatively allow a breast pump funnel portion access to the nipple of its associated breast, each of said slit openings being of an original size; wherein said original size is larger than a female nipple but smaller than the female breast; said slit opening is formed from the said unitary piece of fabric of the said cup portions; and wherein the fabric surrounding and defining each of said openings is made of an elastic material such that the opening is enlarged when the fabric around the opening is stretched and subsequently shrinks back to its original size when the fabric is not stretched;

wherein the size of each of said openings is sufficiently large when said surrounding fabric is stretched for the funnel portion of one of said conventional breast pumps to fit through said slit opening and sufficiently small when its surrounding fabric is not stretched for said wide portion of said funnel portion of said breast pump;

wherein said bra, when worn said funnel portions are between a woman's breasts and said fabric surrounding and defining said openings, and wherein said brassiere frictionally and independently supports each breast said funnel portions with breast pump milk containers attached thereto whereby said breast pump operatively works without the need for additional supporting means.

11. The system of claim 10 wherein said breast milk containers are freezer-ready bags adapted to fit said funnel portion.

\* \* \* \* \*